US012772985B2

(12) United States Patent
Lambert

(10) Patent No.: US 12,772,985 B2
(45) Date of Patent: Oct. 27, 2026

(54) CONTINUOUS RETORT

(71) Applicant: RESEARCH AND DEVELOPMENT SYSTEMS LIMITED, Tyne and Wear (GB)

(72) Inventor: David Severs Lambert, Tyne and Wear (GB)

(73) Assignee: RESEARCH AND DEVELOPMENT SYSTEMS LIMITED, Newcastle Upon Tyne (GB)

( * ) Notice: Subject to any disclaimer, the term of this patent is extended or adjusted under 35 U.S.C. 154(b) by 1220 days.

(21) Appl. No.: 17/795,221

(22) PCT Filed: Sep. 11, 2020

(86) PCT No.: PCT/GB2020/052208
§ 371 (c)(1),
(2) Date: Jul. 25, 2022

(87) PCT Pub. No.: WO2021/048570
PCT Pub. Date: Mar. 18, 2021

(65) Prior Publication Data

US 2023/0054061 A1 Feb. 23, 2023

(30) Foreign Application Priority Data

Sep. 11, 2019 (GB) ..................................... 1913112

(51) Int. Cl.
*A23B 2/22* (2025.01)
*A61L 2/04* (2006.01)
(Continued)

(52) U.S. Cl.
CPC ................ *A23B 2/225* (2025.01); *A61L 2/04* (2013.01); *A61L 2/26* (2013.01); *A23V 2002/00* (2013.01); *A61L 2103/05* (2026.01)

(58) Field of Classification Search
CPC ......... A23B 2/225; A23B 2/22; A61L 2/0023; A61L 2/26; A61L 2202/21; A23V 2002/00; A23V 2300/24; Y02P 60/85
See application file for complete search history.

(56) References Cited

U.S. PATENT DOCUMENTS 3,978,970 A * 9/1976 Reimers ................ A23B 2/001 414/789.5
6,026,891 A * 2/2000 Fujiyoshi ........... F28D 15/0266 165/104.34
(Continued)

*Primary Examiner* — Tiffany T Tran

(57) ABSTRACT

An apparatus for heat treatment of a product, in particular food product, and especially food product in a container such as a can, bottle or plastic pouch is disclosed. The apparatus comprises an unloading and loading section, a first treatment section having an inner wall defining a processing volume within which product is heated, a transfer section and a second treatment section having an inner wail defining a processing volume within which product is cooled, multiple carriers for retaining product during treatment designed to provide multi-stage pressure reductions that collectively reduce the maximum over-pressure within the apparatus to ambient pressure and thereby eliminate the need for sealable pressure doors or gate valves. The loading section incorporates means of linear movement of said product carriers in a continuous fashion. The carriers includes elements to create cavities between or within successive carriers and a plurality of throughapertures to force heat treatment fluid into direct contact with product as it flows from over ambient to ambient pressure. A heat exchanger recovers energy from cooling product and continuously re-applies that energy to heat product.

11 Claims, 12 Drawing Sheets

(51) Int. Cl.
*A61L 2/26* (2006.01)
*A61L 103/05* (2026.01)

(56) References Cited

U.S. PATENT DOCUMENTS

| | | | | |
|---|---|---|---|---|
| 2011/0180232 | A1* | 7/2011 | Lambert | A23B 2/33<br>165/10 |
| 2015/0010679 | A1* | 1/2015 | Strong | A23L 5/15<br>99/468 |

* cited by examiner (a) Typical High-Low Labyrinth Seal Configuration (b) Seal Dimensions and Relative Tooth Axial Position (c) Straight-Through Labyrinth Seal Configuration a) Single and Twin Pouch Carrier b) Vertical Static Slimline Can Product Carrier

CONTINUOUS RETORT

FIELD OF THE INVENTION

The present invention is concerned with retorting apparatus used in the heat treatment of food and pharmaceutical products hermetically sealed within containers, including plastic pouches, trays and pots as well as glass jars and thin walled metallic containers.

BACKGROUND TO THE INVENTION

Products that are contained within sealed packages or containers (also referred to as packs), of whatever nature, generate pressure when they are heated. This pressure is caused by the expansion of any air or other gases present in the container as well as the steam vapour pressure caused by the heating of any water that is present.

The marketplace has been moving away from traditional 'thick wailed' tin cans and glass jars for several decades and is moving towards 'thin wailed' tin and aluminium cans as well as laminated plastic pouches, pots and trays. These new containers are not as strong as traditional tin cans, particularly at elevated temperatures, which has brought challenges to the designers of retort systems.

The Prior Art

There are two main types of retorts, simple cylindrical horizontal pressure vessels with one or two sealable doors to allow the loading and unloading of product, known as batch retorts, and more complex and much larger continuous retort systems. Both have existed for well over 50 years and both have inherent problems when trying to sterilise or pasteurise the new packaging types. In the past 10 years new and innovative retort systems have been developed, such as the microwave assisted sterilisation (MATS), but none has had any significant commercial success.

Batch Retorts

Prior art batch retorts have poor control of individual product temperatures and heat transfer rates, particularly during the heating and cooling stages o he heat process. The lack of control of heat transfer rate is even more of an issue in steam/air batch retorts because dry air at sterilisation temperatures (around 121.5° C.) has 2,500 times less energy per unit volume than steam at the same temperature and transfers energy 24 times more slowly. Work undertaken in 2016 has shown that steam/air retorts, even after the venting process that is designed to remove as much air as possible, still have up to 45% air in pockets during the critical sterilisation stage. Consequently, the thermal process must be undertaken slowly and for an unnecessarily long time resulting in the bulk of the products being significantly over-processed to guarantee that the 'cold spot' products achieve the minimum heat process for food safety. The Food and Drug Administration (FDA) in the United States now insists that all retort systems where air can be in contact with the food packaging (this includes Steam/Air, Water Spray and Water Steam systems) have heat and heat transmission rate distribution as well as temperature distribution work done before the products made on them can be imported into N. America, Because the temperatures and energy transfer rates vary within the pressure vessel of the retort and the pressure has the same value throughout it is impossible to match the varying internal pack pressures with a single over-pressure. The differential pressure thereby created within packs that were either too cold or too hot for the global over-pressure causes stresses and damage within the packaging materials of the container as well as the food stuffs contained therein. Although the over-pressure is variable, it is the same throughout the retort.

Continuous Retorts

Prior art continuous retorts, such as the spiral and reel, hydrostat and hydrolock systems, suffer from a different type of over-pressure problem—they all utilise chambers or vessels within which the over-pressure is a constant, but the product temperatures are rapidly increasing as they pass through the heating chamber, and rapidly decreasing as they pass through the cooling chambers. The overall impact is the same, the product and product packaging undergoes significant pressure differentials during thermal processing that in turn cause stress and deformation of the newer less rigid packaging types and additionally potential product damage through crushing.

The hydrostat type of continuous retort relies on the product entry into the high pressure zone to be done by using a continuous product carrier chain passing through vertical water columns, which are of sufficient height to counterbalance the steam pressure in the sterilisation chamber above the water columns. This means that the retort is often higher than the factory it operates in, in order to retain the over-pressure. High maintenance cost is a major drawback with the principal drive chains costing over $1 m.

Although much more compact and capable of processing up to 5,000 thick walled cans per minute, Spiral and Reel retorts require the packs containing the products to be cylindrical in shape, as well as being very strong in order to be able to pass through the system or to be small enough to be enclosed within robust cylindrical carriers. Once manufactured, such retorts are also limited to containers with the same overall dimensions and are also expensive to maintain.

Spiral and Reel retorts have inlet and outlet ports that are airlocks through which the product enters and exits the pressure vessels. This system entrains air as the product enters the retort and vents have to be incorporated in the retort to continuously expel a mixture of steam and air to minimise retained air. This system is energy inefficient and causes condensation within the factories.

The Hydrolock type of continuous retort is a large batch retort type pressure vessel through which passes a continual product carrier chain holding product within cylindrical carriers. The upper part of the pressure vessel is filled with saturated steam at the desired sterilisation temperature, and the lower section is filled with cold water.

The loaded product-carrying chain enters the pressure vessel and is heated by the steam before descending into the cold water which cools the product before exiting the pressure vessel ready to be unloaded.

Both the Spiral and Reel and the Hydrolock continuous retorts suffer from another serious problem; the pressure it the sterilising vessel and the cooling vessel is around 2.7 barg in order to allow the elevated temperatures, but the products entering the sterilising vessel and leaving the cooling vessel are relatively cold, with virtually no internal pressure. This can cause crushing of the product container.

Both of these continuous retorts can have pre-heaters and second stage cooling, but this only slightly diminishes the crushing through pressure differential problems, Retort Packaging Most plastic packaging that is designed for thermal processing and microwave heating by the consumer utilises either silicon oxide or aluminium oxide coatings to provide an oxygen barrier. These coatings break down if the base material is stretched more than 4%, so the differential pressure problems can affect the quality of the contents of the packs as well as reducing the product shelf life. In extreme cases, if the differential pressure becomes too high the seals in the packs can fail, allowing harmful bacteria to recontaminate the contents after processing, which is a major food safety issue.

Whilst excess internal pressure, or insufficient over-pressure is the main problem, too much over-pressure can crush the container with the potential consequences of squashed product, deformed containers and ruptured seams or seals.

Batch retorts provide better over-pressure control than prior art continuous retorts and so have become more popular for products using the new retort packaging materials, but their slower processing speeds require large numbers of retorts to meet the throughput requirements of most large processors, typically 400 containers per minute. Additionally, the loading and unloading systems of the large cuboid baskets used in these retorts are complex and expensive. The combination of the large number of these batch retorts with the associated product handling system takes up significantly more factory space than prior art continuous retorts.

Whilst prior art continuous retorts operate at the required speed with relatively small footprints, their inherent lack of controlled and variable over-pressure makes them unsuitable for most plastic containers as well as thin walled tin and aluminium cans.

Gas Injection of Retort Packaging

The increasing popularity of liquid nitrogen infused ‘ready to drink’ (RTD) products in thin walled aluminium cans that require thermal processing, demands significantly higher over-pressure to avoid the hot nitrogen gas pressure formed, causing the thin-walled cans to deform or even explode. Liquid nitrogen boils at −196° C. and at typical infusion rates can generate internal pressures exceeding 9 barg at 121.5° C. requiring retort overpressures exceeding 4 barg. Temperature and pressure variations in existing technology batch retorts cause higher risk of can rupture in these products.

The present invention therefore seeks to address the above problems by ensuring that the product temperatures in discrete sections are the same and by enabling the internal retort pressure in each of these discrete sections to be different and to be controlled in such a way as to always be the correct over-pressure for all product temperatures in a continuous retort system.

Full Immersion Water Versus Steam/Air or Water Spray Retorts

The significant differences in energy state and insulation properties of air, water and steam mean that air should be considered to be a real danger in any retort system, and so a full immersion water system is preferable as this is the only retort technology capable of guaranteeing that there will be no or minimal air present.

Although there are many prior art full immersion water batch retorts in common use there are no full immersion continuous retorts.

The full immersion batch retorts suffer from two drawbacks; a) they need to use very large quantities of water, all of which needs to be heated and cooled in addition to the metalwork of the retort pressure vessel and pipework and the product being sterilised, so they are energy inefficient, and: b) they suffer from the other problems of all batch retorts in that the product is processed in large diameter cylindrical pressure vessels where the product itself is processed in large cuboid baskets within which heat transfer is poor and variable.

The present invention solves these additional problems by: a) minimising pipework as well as eliminating all non-product containing volumes, and: b) adopting a radically different retort design—rather than contain the product in several large cuboid baskets within a large-diameter cylindrical pressure vessel with sealable doors to contain the overpressure, the product is housed in small cylindrical carriers within long, small-diameter pressure vessels with no doors or gate valves. In this invention the multitude of cylindrical product carriers collectively act as the sealing mechanism, with each carrier creating a fractional pressure drop, the sum of which pressure drops equals the full retort overpressure.

Typical cuboid baskets in existing technology batch retorts contain several hundred or even thousands of products. The small cylindrical carriers of the current invention typically carry fewer than 100 products.

The technology adopted to provide the necessary pressure seal, but still allow free product carrier entry and exit, is similar to that of the modular control valve or the labyrinth seals on steam turbines, where the total overpressure is divided into multiple small pressure drops, such pressure drops also providing the motive force to create the desired forced convective water flow.

In a typical device shown in FIG. 1, a multiple 4-stage valve spindle 30 divides the pressure difference ($P_i$-$P_0$) to drop the pressure by a factor of 4 and eliminate cavitation.

By causing the heat transfer fluid to be forced past the products contained within small product carriers, every product receives the same amount of energy as well as the same driving temperature.

Each product carrier acts as the valve seat on the multiple stage valve and the teeth of the labyrinth seal in the turbine. Examples of this are shown in FIG. 2.

In the present invention, the individual product carrier incorporates through apertures to regulate and distribute the heat transfer fluid to direct the heating to the product surfaces, whether or not product is present within the product carrier. The given pressure drop for any given fluid flowrate is therefore independent of the presence or absence of product at any given location within the treatment chamber. In the embodiment of FIG. 3, 12 individual product carriers 40 in each pressure vessel 41 divide the total pressure difference in pressure, ($P_{max}$−$P_{min}$) to drop the pressure by a factor of 20. This aspect enables gate valves, which are normally utilised to be dispensed with in the apparatus of the present invention. FIG. 3 shows a relative size of the product carriers 40 to the walls of the pressure vessels 41 and 42 with the length of the pressure vessels 41 and 42 being approximately 12 times the diameter of the pressure vessels and the diameter of the product carriers 40 being almost the same as the diameter of the pressure vessels 41 and 42.

Individual sector pressure can be controlled and regulated using injection, bypass or exhaust manifolds (See element 45 of FIG. 4) mounted on the outside of the treatment chambers linked to other sources of fluids with the required conditions using control valves, Finally, this invention shows how this continuous retort can recover and re-apply nearly all the energy used in heating and cooling the water as well as the product in the full immersion system thereby saving both steam energy and cooling water.

The heat exchange fluids that pass from the high pressure sterilisation section to the ambient pressure loading section are forced to pass around the product in counterflow as the product carriers are progressively moved from the loading section towards the sterilisation section. As the cold product moves from said loading section toward said sterilisation section the heat transfer fluid flowing in counterflow is cooled toward ambient temperature. This feature of the continuous retorting apparatus is facilitated by the flow direction of the product being in counterflow to the flow direction of the heat transfer and the respective heating of product and cooling of fluids work in the desired sense.

The recovery of energy, however, is more difficult because the product being cooled in the cooling section as it moves from the high pressure sterilisation section towards the ambient pressure unloading section is moving in the same direction as the high temperature water leaving said sterilisation section as it flows toward said ambient pressure section.

In order to enable heat recovery, a fluid stream flowing over the products in the product carriers that are being cooled has to move in counter-flow to the direction of the product carriers. This requires a novel type of heat exchanger to be employed whereby the two fluid flows can each be managed in the sense required by the apparatus.

This invention incorporates a mufti-stage contra-flow heat exchanger to manage the product cooling fluid in counter flow to the product at the same time as the high temperature fluid leaving said sterilisation sector flowing in the same sense as the product.

FIG. 5 illustrates diagrammatically a suitable heat exchange set-up. In the Figure, the large arrow A indicates the direction of travel of product carriers in a cooling sector 50 during cooling, as they move from a first, high temperature/high pressure region 51 towards a low temperature/low pressure region 52. A plurality of manifolds 56 links the product carriers in the cooling sector 50 with cooling fluid which flows along cylinders 53, 54 and into the cooling sector 50 via the manifolds 56. Once the cooling fluids have passed across the product carriers, the cooling fluids exit the cooling sector 50 by a further one of the manifolds 56 to flow further along the cylinder 54 in the direction of the arrow 58. The cylinders 53 and 54 are separated by a wall 55. This ensures the cooling fluid is diverted through into the cooling sector 50. A central core 57 carries the contraflow cooling fluid which removes heat from the fluids passing through the cylinders 53 and 54. FIG. 5 shows a relative diameter of the product carriers 40 compared to the diameter of the pressure vessel 42 as well as the small gap that is left between the two through which the heat treatment liquid has to pass.

SUMMARY OF THE INVENTION

According to the invention, there is provided an apparatus for heat treatment of a product, in particular food product, and especially food product in a container such as a can, glass bottle or plastic container, tray or pouch, the apparatus comprising a Loading Section, a First Treatment Section, the First Treatment Section having a wall defining a generally tubular processing volume within which Product is heat treated, a Transfer Section, a Second Treatment Section, the Second Treatment Section having a wall defining a generally tubular processing volume within which Product is cooled, and an Unloading Section adjacent to said Loading Section;

- multiple Product Carriers moving sequentially through the various sections for retaining product during treatment pushed by a propelling means;
- a Product Carrier being so shaped to define at least one cavity between itself and a Treatment Section;
- said Product Carriers including throughapertures to provide water channels surrounding Product being heat treated and direct water onto a Product surface;
- pumps, heat exchangers, valves, manifolds and conduits within which heat treatment fluids are transported between different locations within the Treatment Sections.

Preferably, the propelling means incorporates rotation means engaging linkage means on a Product Carrier to enable product to be rotated to ensure even heat treatment of the product. Further preferably, a Product Carrier includes further linkage means to engage corresponding linkage means on an adjacent Product Carrier to facilitate the rotation mechanism.

Preferably, the propelling means is a piston or linear drive, and further preferably a piston. Further preferably, the apparatus includes a spiral bar, operably rotatably linked to the piston, rotation of the spiral bar causing rotation of the piston.

Optionally, the apparatus includes at least one Multi-stage Contra-flow Heat Exchanger to at least partially recover energy from the cooling of Product.

Preferably, at least one Magnetron to transmit microwave energy to assist in the heating of Product.

Preferably, a Treatment Section includes double jackets within which heat transfer fluids or gases can circulate.

Conveniently, a Product Carrier is 3D printed or machined from a high temperature polymer to aid in rapid manufacture and/or obtention of replacement parts.

According to a second aspect of the invention there is provided an apparatus for heat treatment of a product, in particular food product, and especially food product in a container such as a can, bottle, tray or plastic pouch, the apparatus comprising a loading section, the loading section having an inner shuttle system to enable product carriers to be sequentially loaded into at least one tubular treatment section by means of a loading piston;

- the tubular treatment section having an inner wall defining a processing volume within which product is treated;
- multiple product carriers are arranged to pass through the tubular treatment section for retaining product during said treatment with each product carrier being pushed by the preceding product carrier and in turn by said loading piston;
- said loading piston being able to remain rotationally static or rotate along the longitudinal axis of said tubular treatment section;
- said loading piston engaging with said product carrier with lugs and recesses such that rotation of said loading piston causes rotation of said product carrier;
- each product carrier incorporating lugs and recesses to engage with each sequential product carrier so that rotation of one product carrier is transmitted to all product carriers
- each product carrier incorporating recesses to engage with restraining means located within said tubular treatment section;
- said product carriers include multiple product chambers within which product is contained;
- hollow recesses and channels surrounding the individual product chambers allowing fluid-flow path about said product;
- the treatment section having at least one end connected to at least one transfer section;

the transfer section having an inner shuttle system to enable said product carriers to be sequentially removed from the first treatment section; and be transferred to a second treatment section;

the second treatment section having an inner wall defining a processing volume within which product is treated within said product carriers;

said second treatment section having at least one end connected to at least one unloading section;

said unloading section allowing product to be sequentially removed from said product carriers and including a product carrier shuttle system connected to said loading section allowing newly emptied product carriers to be loaded prior to entering said first treatment section;

there are no sealable doors or gate valves between the sections describe herein that would otherwise make them chambers rather than sections.

Each individual product carrier acts as a small batch retort with changing thermal and pressure properties as it is moved through the heating section to the sterilisation section and finally the cooling section, with the heat exchange fluid continually leaking from the said small batch retort and being continually replenished with higher pressure heat exchange fluid at the required temperature.

BRIEF DESCRIPTION OF THE DRAWINGS

The invention is now described with reference to the accompanying drawings, which show by way of example 3 embodiments of a retort apparatus and three embodiments of a product carrier. In the drawings.

DETAILED DESCRIPTION OF THE INVENTION

Figure 1:
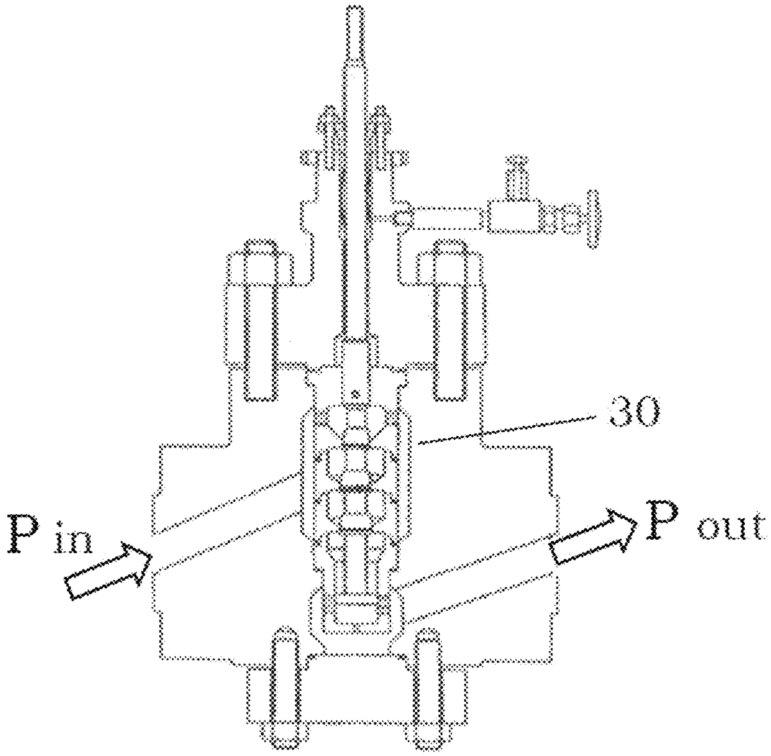
FIG. 1 illustrates a typical multi--stage pressure reduction control valve.
Figure 2:
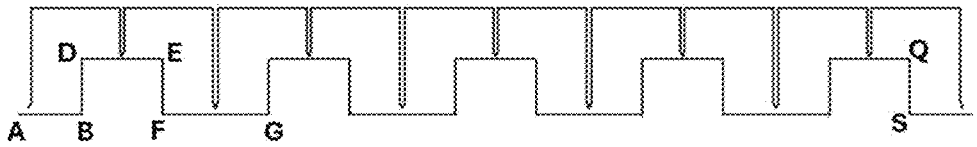
FIGS. 2*a*-2*c* illustrate typical steam turbine labyrinth seal arrangements.
Figure 2:
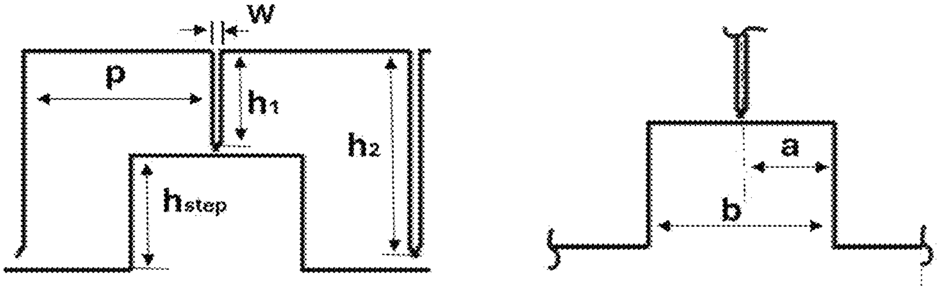
Figure 2:
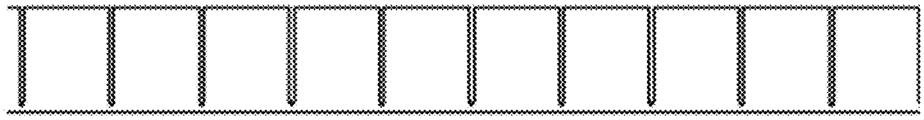
Figure 3:
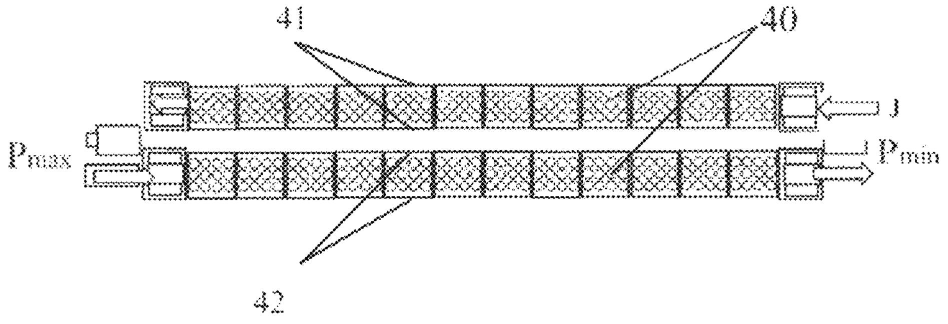
FIG. 3 illustrates multi-stage pressure reduction using multiple product carriers.
Figure 4:
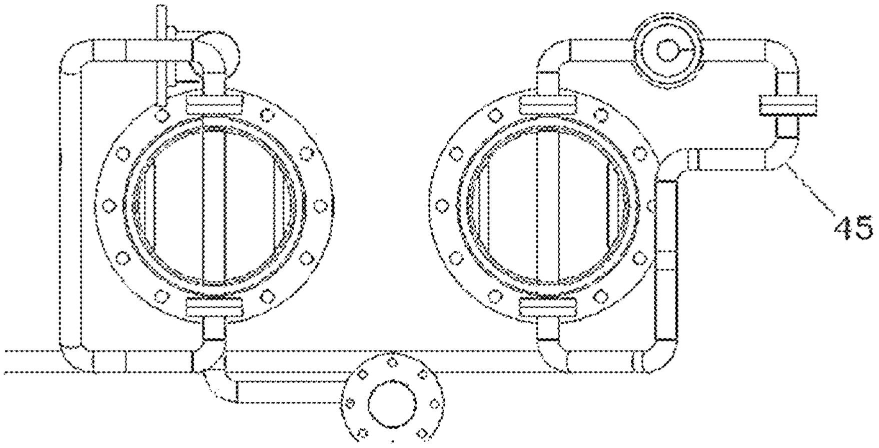
FIG. 4 illustrates external manifolds linked to treatment chambers.
Figure 5:
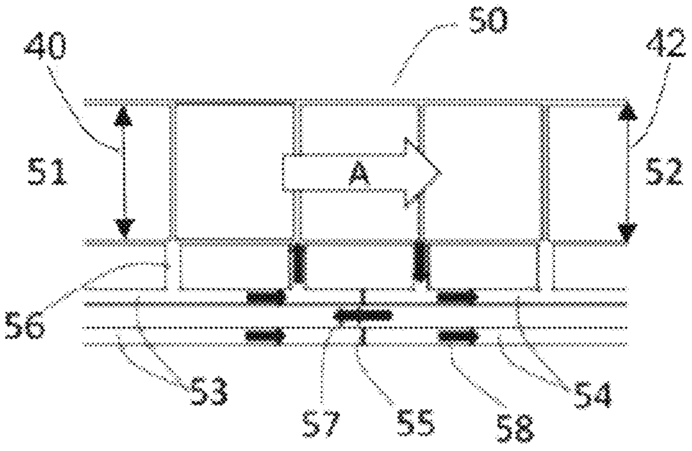
FIG. 5 illustrates external manifolds linked to a multi-stage contraflow heat exchanger.
Figure 6:
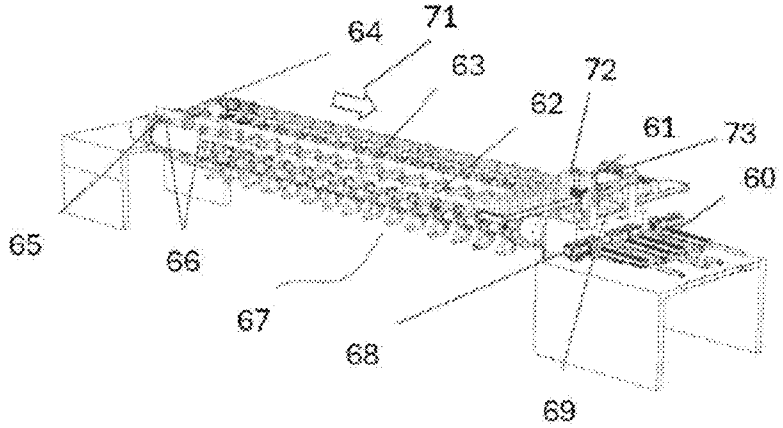
FIG. 6 illustrates a continuous retort apparatus with two treatment sections with linear transfer sections.
Figure 7:
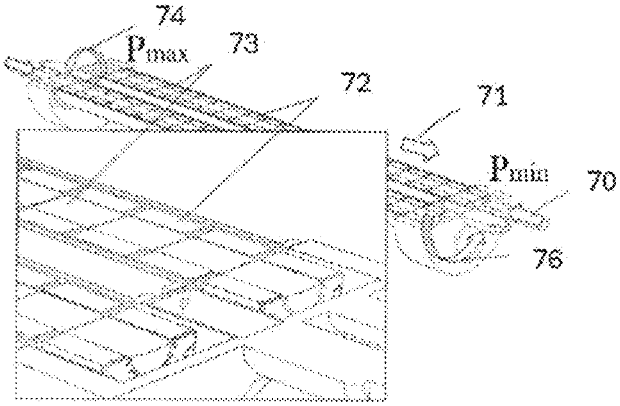
FIG. 7 illustrates sectional views of another type of two section continuous retort apparatus with rotary transfer sections.

As set out above, prior art batch retorts suffer from a number of disadvantages, such as inaccurate processing, particularly with steam/air or steam/water retorts, low processing speed, complex loading and unloading systems and a large overall apparatus footprint for any given throughput. Further, full-immersion water batch retorts use very large quantities of water and energy.

Prior art continuous retorts have high throughputs for any given footprint but suffer from insufficient variability of pressure control during heating and cooling. In addition, spiral and reel continuous retorts are inflexible in relation to different product sizes and are energy inefficient due to the need to continually vent steam in order to remove entrained air.

The present invention seeks to address these problems through the provision of a continuous retort apparatus having fully variable over-pressure during all treatment phases with the ability to easily size change between product of differing sizes and shapes. The apparatus can heat treat all types of retort packaging at high as well as low throughputs within a small footprint and in a highly energy efficient way.

In a preferred embodiment, the present invention is also designed to be used in conjunction with magnetrons to further increase throughput using microwave energy in addition to convective and conductive heat energy in order to minimise the damage to flavour, nutrition, texture and appearance a caused by thermal processing where the product is contained within non-metallic packaging and the product carriers are manufactured from non:-metallic materials such as 3D printed thermoplastics. In the hereindescribed embodiment, magnetrons are illustrated as being attached to a Transfer section to effect heating of product therein. However, magnetrons can be utilised at other stages of the heating process to provide rapid and localised heating and cost-effective heating.

The apparatus 67 in its simplest form and with reference to FIGS. 6-9, comprises four fully-flooded modules as follows:

a Loading Section 61 within which individual Product Carriers 73 are loaded with Product 72, prior to transferring, by the action of a Loading Piston 60 or other loading means in the direction shown by the arrow 70 to;

a First Treatment Section 62 for the heating of Product 72 within which successive Product Carriers 73 are aligned along the central longitudinal axis of said First Treatment Section 62 such that as each new Product Carrier 73 is introduced into a Product Carrier aperture 69 from said Loading Section 61 all Product Carriers 73 within said First Treatment Section 62 are moved along the said central longitudinal axis away from said Loading Section 6:1 towards and against the pressure gradient 71;

a Transfer Section 64 where Product Carriers 73 are transferred in the direction shown by the arrow 74, and within which individual Product Carriers 73 are pushed from said First Treatment Section 62 by the action of said Loading Piston 60 within said Loading Section 61 prior to being transferred by the action of a Rotary Transfer Motor 68, Linear Piston or other means to align with the central longitudinal axis of;

a Second Treatment Section 63 for the cooling of Product 72 within which successive Product Carriers 73 are aligned along the central longitudinal axis of said Second Treatment Section 63 such that as each new Product Carrier 73 is introduced from said Transfer Section 64 by a Return Piston 65 or other means, all Product Carriers 73 within said Second Treatment Section 63 are moved along the said central longitudinal axis away from said Transfer Section 64 towards an Unloading Section connected to said Loading Section 61 within which Product 72 that has been heat treated is unloaded prior to said Product Carrier 73 being loaded with untreated Product 72, thereby completing the continuous circuit.

At least one Fluid Inlet 66 at the Transfer Section 64 end of each Treatment Section 62, 63 allows hot or cold water to enter the Treatment Sections 62, 63 at the required pressure that will provide pressure equilibrium within said Product Packaging at the temperature the Product 72 has achieved at that position.

At least one Fluid Outlet at the Loading and Unloading Section 61 end of each Treatment Section 62, 63 allows hot or cold water to exit said Treatment Sections 62, 63 at the required pressure that will provide pressure equilibrium within said Product packaging at the temperature the Product 72 has achieved at that position.

As the pressure of the hot or cold water entering each Treatment Section 62, 63 via said Fluid Inlet 66 is always higher than the pressure of the hot or cold water leaving said Treatment Sections 62, 63 there is created a Pressure Gradient 71 which causes the continuous flow of hot or cold water from said Fluid Inlets 66 towards said Fluid Outlets.

Pressure and temperature measurement means located along the length of said Treatment Sections 62, 63 provide feedback to the retorting apparatus' artificial intelligence or other control system and further fluid inlets and outlets located along the length of said Treatment Sections 62, 63 allow localised increases and decreases in the pressure of the hot or cold water according to the temperature profile of the Product 72 as it passes through said Treatment Sections 62, 63 from said Loading Section 61 towards said Transfer Section and back again. Once emptied, a Product Carrier 73 is rotated at 76 back to the Loading Section 6:1 ready to receive further Product 72.

Figure 8A:
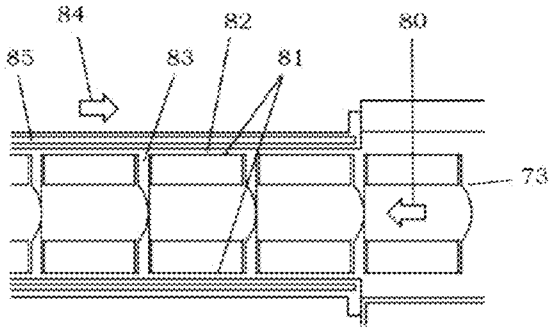
FIGS. 8*a*, 8*b* illustrate sectional views of the product carriers within a treatment section.
Figure 8B:
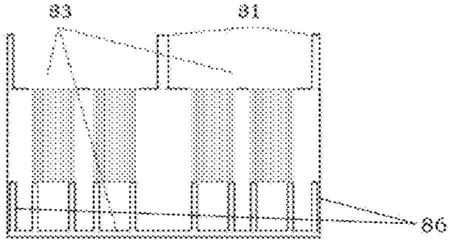

In FIGS. 8, Product Carriers 73 are shown moving within a treatment section having a double jacket 85. Between the II of the retort and the product Carriers 73 is maintained an inner water gap 82. Each Product Carrier incorporates at least one raised section or element 81 to create a gap between said Product Carrier 73 and its adjacent Product Carrier 73, and said gap creates a Cavity 83 between successive Product Carriers 73 that act as manifolds to help distribute said hot or cold water in the most effective manner for heat transfer as well as the insertion of restraining means 86 as successive loading and unloading pistons return for the next Product Carrier 73.

Alternatively, the top and bottom surfaces of said product carriers include a plurality of throughapertures 92 such that each product carrier in said alternative arrangement is in direct fluid contact with each adjacent product carrier and has baffles so arranged as to redirect said axial flow of water vertically downward or vertically upward around each product.

Alternatively, the raised elements 81 create cavities 83 to act as manifolds directing heat transfer flows that are perpendicular to the axis of the treatments sections.

Throughapertures within said Product Carriers 73 are such that as the Product Carriers 73 move in the direction of the arrow 80, the throughapertures allow said hot or cold water that is moving in the direction of said Pressure Gradient 84 and which gathers in the Cavity 83 to pass around said Product and thereby heat or cool said Product, or in the alternative gathers in the Cavity 83 above or below the product where the water flow is vertical.

By way of example, if the maximum temperature and pressure of the heating water is 140° C. and 3 Barg and the minimum temperature and pressure is 20° C. and ambient and there are 12 Product Carriers in the intermediate zone between these two sets of conditions the temperature difference between each Product Carrier will be approximately 10° C. and the pressure gradient across each Product Carrier to force the heating water past the Product contained in said Product Carrier will be 0.25 barg. Although the Product Carriers and associated sections can be of any cross-sectional shape, the preferred configuration utilises cylindrical Product Carriers moving through cylindrical sections in order to allow rotation of the product carrier about the longitudinal axis of the tubular treatment section if so desired.

Figure 9:
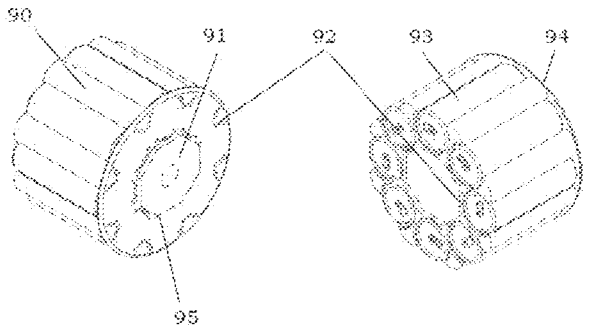
FIG. 9 illustrates a Product Carrier.
Figure 10:
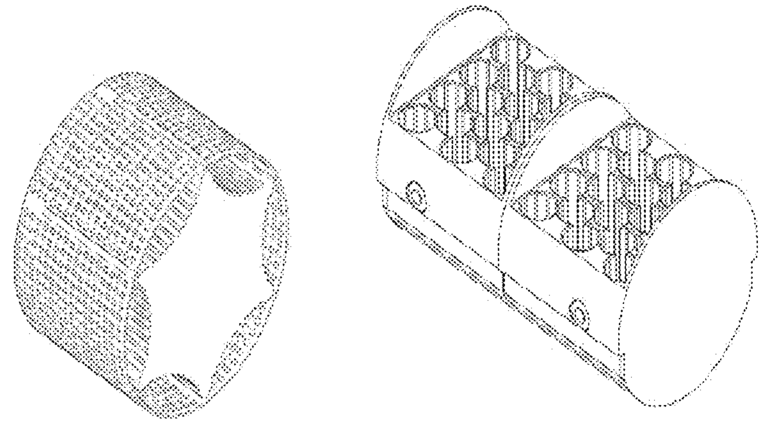
FIGS. 10*a* and *b* illustrate types of product carrier.

In a preferred embodiment of the present invention, and referring to FIGS. 9, each Product Carrier 90, containing Product 93, incorporates at least one disc 94 which has a greater outside dimension than the body of said Product Carrier 90 to create an area of high speed turbulent water flow.

In a further preferred embodiment of the present invention said discs 94 incorporate linkage means comprising raised sections and recesses 95 to allow the transmission of rotary torque action to transmit rotation from the Loading Piston 60 to each successive Product Carrier 90 such that when said Loading Piston 60 rotates then all Product Carriers 90 connected to it preferably also rotate. The cavities or water channels 92, as described previously are shown. In alternative embodiments, a linear drive can be used as propelling means instead of a piston. Other means known in the art can, less preferably also be utilised.

In one embodiment of the invention, the Loading Piston 60 is connected to a spiral bar, the spiral bar typically comprising a spiral having a 360° turn or greater. In one embodiment, an actuator releasably locks the spiral bar against rotation, and upon translational motion of the Loading Piston 60, the spiral bar does not rotate. Where rotation of the Loading Piston 60 is required, the actuator is released, and as the piston undergoes translation, the spiral bar is caused to rotate, and in so rotating causes the Loading Piston to also rotate. This action therefore acts also to rotate the Product Carriers in the manner described herein. The inclusion of a 360° spiral on the spiral bar results in the Loading Piston 60, and hence the Product Carriers undergoing one full rotation as they traverse the apparatus.

In a further preferred embodiment of the present invention each Treatment Section 62, 63 incorporates a double jacket 85 within which heat transfer fluids or gases can circulate to either heat or cool the inner wall of said Treatment Section 62, 63.

In yet a further preferred embodiment of the present invention energy gained by the heat transfer fluids during cooling of Product in one Treatment Section is transferred to the heat transfer fluids used in heating Product in another Treatment Section via a heat exchanger.

In a yet further preferred embodiment of the present invention said heat exchanger is a mufti-stage contra-flow heat exchanger In yet a further preferred embodiment of the present invention Product Carriers are manufactured from high-temperature polymers .such as Peek and Pekk using 3D printing techniques.

In yet a further preferred embodiment of the present invention at least one Magnetron microwave energy generator is incorporated within at least one Transfer Section such that when the retort apparatus is processing Product in non-metallic packaging contained in said 3D printed polymer Product Carriers microwave energy from said Magnetron can be used to assist the heat transfer fluids in heating the Product as the Product Carrier is rotated.

Figure 11:
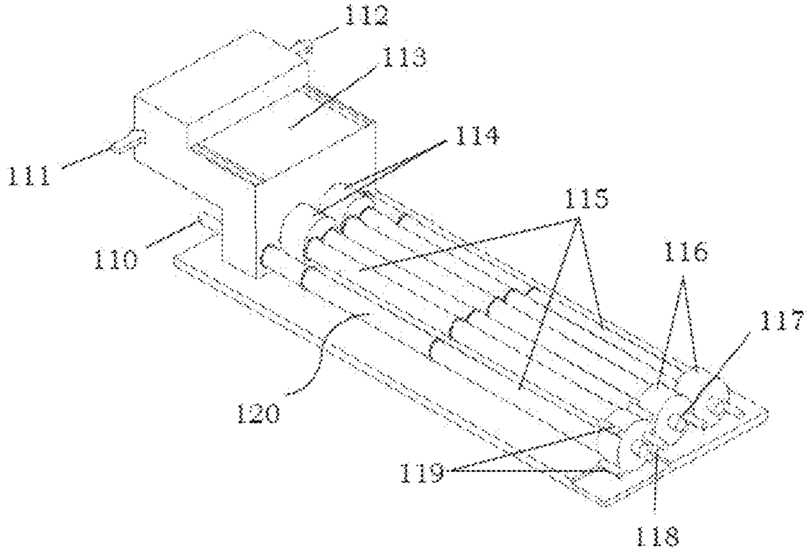
FIG. 11 illustrates a 12 tube, 6 treatment section continuous retort apparatus.

In FIG. 11, a 12 tube, 6 treatment section continuous retort apparatus 1.20 is disclosed, which incorporates means to provide said microwave heating. Product enters the apparatus in the loading section 111. The loading system 113 transfers the product to a carrier, which are then urged into position by means of the loading piston 110. The product then passes along the outermost tube of the treatment section 115, as described above, and undergoing part of the heat treatment, until it reaches the first of the transfer sections 116. The product is rotated within the transfer section 116 to bring it into alignment with one of the neighbouring treatment sections 115. The rotation is driven by transfer motors 117. During the rotation in the transfer section 116, microwave energy is transferred to the product from the magnetrons 119 arrayed on the outside of the transfer sections 116. A return piston 118 then urges the product into alignment for travel along the next stage of the treatment section 115. Treatment continues within the apparatus in a similar fashion, A second array of transfer sections 114 is provided at the opposite ends of the transfer section 115. On completion of the treatment, product leaves the apparatus via the unloading section 112.

Figure 12:
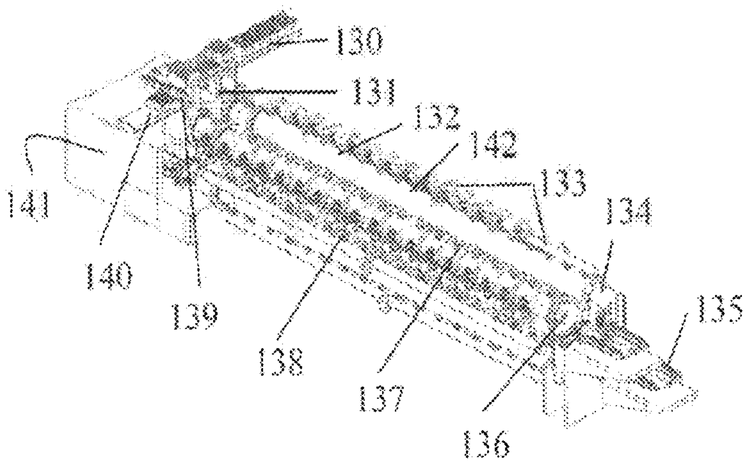
FIG. 12 illustrates a 4 tube continuous retort apparatus with full heat recovery.

In FIG 12, is shown a 4 tube continuous retort apparatus 141 with full heat recovery, in which two of the tubes are arrayed over the other 2 tubes to provide a more compact structure and to facilitate control of heat energy with in the apparatus. Product is brought into the loading station 131 of the apparatus by the conveyor 130. The product is then transferred to the first of the four tubes of the primary heating section 132 which operates in the manner described above to heat product to the desired temperature in a safe and efficient manner. Product continues along the tube 142 of the primary heating section 131 until it reaches the first vertical transfer station 134. The product is transferred downwards and aligned with a second tube by the second stage piston 135. Passage along the second tube then takes place, and on reaching the end of the second tube, the product is transferred sideways to a third tube and passes along this tube until the product reaches the second vertical transfer station 136 which lifts the product and brings the product to the first end of the fourth tube for the final stage of the heat treatment, cooling the product ready for the product to be unloaded in the unloading section 139. The treated product is transferred to the unloading conveyor 140 to be packaged.

In order to maximise the use of heat energy, the apparatus is provided with a conduit and manifold system 133 to transfer heat from sections of the apparatus 141 where there is excess heat energy, to where the heat energy is required. multi-stage counter-flow heat exchanger 137 is provided to increase heat efficiency. A secondary cooling system 138 is also provided should it be required.

What is claimed is:

1. An apparatus for a heat treatment of a product by a heat treatment liquid, the apparatus comprising:

a Loading Section, a First Treatment Section, wherein the First Treatment Section having a wall defining a generally horizontally deployed pressure vessel within which the product is heat-treated, a Transfer Section, a Second Treatment Section, wherein the Second Treatment Section having a wall defining a generally horizontally deployed pressure vessel within which the product is cooled, and an Unloading Section adjacent to said Loading Section, wherein either one of the First Treatment Section and the Second Treatment Section pressure vessels having no doors or gate valves;

multiple Product Carriers moved sequentially through all of the sections for retaining the product during the heat treatment by pistons or linear drives;

each Product Carrier of the multiple Product Carriers being sized to restrict the flow of the heat treatment liquid between said multiple Product Carriers and the said wall of each of the First Treatment Section and Second Treatment Section and thereby create a fractional drop in pressure of the heat treatment liquid over each one of the said multiple Product Carriers, the number of the multiple Product Carriers required in each of the First Treatment Section and Second Treatment Section being equal to a required total pressure drop across each Treatment Section divided by the fractional drop in pressure over each product carrier of the multiple Product Carriers rounded up to the next whole number;

the apparatus including restraining means insertable between the multiple Product Carriers when said pistons or linear drives retract ready for the next pushing cycle;

said multiple Product Carriers including through apertures to provide water channels surrounding the product being heat treated and direct water onto a surface of the product;

pumps, heat exchangers, valves, manifolds, and conduits within which the heat treatment liquid is transported between different locations within said First Treatment Section and said Second Treatment Section.

2. The apparatus in accordance with claim 1, wherein the pistons or linear drives incorporate rotators engaging linkages on said multiple Product Carriers.

3. The apparatus according to claim 2, wherein each of the multiple Product Carriers includes further linkage means to engage corresponding linkages on each of said multiple Product Carriers that is adjacent to said multiple Product Carriers aforementioned.

4. The apparatus according to claim 2, wherein the rotator includes a spiral bar, mounted for rotation and operably linked to rotate the pistons or linear drives as the spiral bar rotates.

5. The apparatus in accordance with claim 1, wherein the apparatus includes at least one Multi-stage counter-flow Heat Exchanger to recover energy from the cooling of the product in said second Treatment Section and transfer said energy to aid the heating of the product in said First Treatment Section.

6. The apparatus in accordance with claim 1, incorporating at least one Magnetron to transmit microwave energy to assist in the heating of the product.

7. The apparatus in accordance with claim 1, wherein either of the First Treatment Section or Second Treatment Section includes double jackets within which heat transfer liquids or gases circulate.

8. The apparatus in accordance with claim 1, wherein the multiple Product Carriers are 3D printed or machined from a polymer.

9. The apparatus in accordance with claim 1, wherein the pressures within the First Treatment Section and Second Treatment Section are controlled and regulated using manifolds mounted on the outside of the said treatment sections linked to other sources of heat treatment liquids incorporating control valves.

10. The apparatus in accordance with claim 1, wherein said First Treatment Section, Second Treatment Section and said multiple Product Carriers are cylindrical in cross section.

11. The apparatus according to claim 1, wherein each product carrier of the multiple Product Carriers incorporates recesses to engage with restraints located within said First Treatment Section and Second Treatment Section.

* * * * *